United States Patent
Koll et al.

(10) Patent No.: US 9,996,510 B2
(45) Date of Patent: *Jun. 12, 2018

(54) DOCUMENT EXTENSION IN DICTATION-BASED DOCUMENT GENERATION WORKFLOW

(71) Applicant: MModal IP LLC, Franklin, TN (US)

(72) Inventors: Detlef Koll, Pittsburgh, PA (US); Juergen Fritsch, Pittsburgh, PA (US); Michael Finke, Pittsburgh, PA (US)

(73) Assignee: MModal IP LLC, Franklin, TN (US)

( * ) Notice: Subject to any disclaimer, the term of this patent is extended or adjusted under 35 U.S.C. 154(b) by 293 days.

This patent is subject to a terminal disclaimer.

(21) Appl. No.: 15/055,069

(22) Filed: Feb. 26, 2016

(65) Prior Publication Data

US 2016/0179770 A1 Jun. 23, 2016

Related U.S. Application Data

(63) Continuation of application No. 14/326,971, filed on Jul. 9, 2014, now Pat. No. 9,275,643, which is a (Continued)

(51) Int. Cl.
*G10L 15/20* (2006.01)
*G06F 17/22* (2006.01)
(Continued)

(52) U.S. Cl.
CPC .......... *G06F 17/2247* (2013.01); *G06F 3/167* (2013.01); *G06F 17/24* (2013.01);
(Continued)

(58) Field of Classification Search
CPC .......... G10L 15/20; G10L 15/22; G10L 15/26
(Continued)

(56) References Cited

U.S. PATENT DOCUMENTS 5,148,366 A * 9/1992 Buchanan ............. G06F 17/243
707/999.009
5,823,948 A 10/1998 Ross et al.
(Continued)

FOREIGN PATENT DOCUMENTS

EP 1361522 A2 11/2003
JP H09106428 A 4/1997
(Continued)

OTHER PUBLICATIONS

Adam E.J.et al., "ESR guidelines for the communication of urgent and unexpected findings" European Society of Radiology (ESR), 2011, vol. 3, Issue (1), pp. 1-3.
(Continued)

*Primary Examiner* — Michael N Opsasnick
(74) *Attorney, Agent, or Firm* — Blueshift IP, LLC; Robert Plotkin (57) ABSTRACT

An automatic speech recognizer is used to produce a structured document representing the contents of human speech. A best practice is applied to the structured document to produce a conclusion, such as a conclusion that required information is missing from the structured document. Content is inserted into the structured document based on the conclusion, thereby producing a modified document. The inserted content may be obtained by prompting a human user for the content and receiving input representing the content from the human user.

20 Claims, 5 Drawing Sheets

Related U.S. Application Data continuation of application No. 13/527,347, filed on Jun. 19, 2012, now Pat. No. 8,781,829.

(60) Provisional application No. 61/498,586, filed on Jun. 19, 2011.

(51) Int. Cl.
  *G10L 15/22* (2006.01)
  *G10L 15/26* (2006.01)
  *G06F 3/16* (2006.01)
  *G06F 17/24* (2006.01)

(52) U.S. Cl.
  CPC .............. *G10L 15/22* (2013.01); *G10L 15/26* (2013.01); *G16H 15/00* (2018.01); *G10L 2015/228* (2013.01)

(58) Field of Classification Search
  USPC ........ 715/201, 209, 277, 817, 825; 704/235, 704/10
  See application file for complete search history.

(56) References Cited

U.S. PATENT DOCUMENTS

| | | | |
|---|---|---|---|
| 6,006,183 A | 12/1999 | Lai et al. | |
| 6,345,249 B1 | 2/2002 | Ortega | |
| 6,377,922 B2* | 4/2002 | Brown .................... | G10L 15/22 379/88.01 |
| 6,738,784 B1 | 5/2004 | Howes | |
| 6,834,264 B2 | 12/2004 | Lucas | |
| 7,379,946 B2 | 5/2008 | Carus | |
| 7,447,988 B2* | 11/2008 | Ross ..................... | G06F 19/328 715/221 |
| 7,519,529 B1 | 4/2009 | Horvitz | |
| 7,584,103 B2* | 9/2009 | Fritsch ................ | G10L 15/1815 704/257 |
| 7,613,610 B1* | 11/2009 | Zimmerman .......... | G06Q 50/22 379/88.01 |
| 7,716,040 B2* | 5/2010 | Koll ....................... | G06F 17/211 704/9 |
| 7,869,998 B1* | 1/2011 | Di Fabbrizio .......... | G10L 13/00 704/1 |
| 8,024,196 B1* | 9/2011 | Wodtke ............... | H04M 3/4938 379/90.01 |
| 8,583,439 B1* | 11/2013 | Kondziela ............. | G10L 15/22 379/189 |
| 8,781,829 B2* | 7/2014 | Koll ....................... | G10L 15/22 704/235 |
| 9,275,643 B2* | 3/2016 | Koll ....................... | G10L 15/22 |
| 9,424,523 B2 | 8/2016 | Koll | |
| 9,679,077 B2 | 6/2017 | Jaganathan et al. | |
| 9,704,099 B2 | 7/2017 | Koll | |
| 2001/0042080 A1 | 11/2001 | Ross | |
| 2002/0065854 A1 | 5/2002 | Pressly | |
| 2002/0077819 A1* | 6/2002 | Girardo ................ | G10L 25/69 704/260 |
| 2002/0099717 A1 | 7/2002 | Bennett | |
| 2004/0044546 A1* | 3/2004 | Moore .................. | G06F 19/325 705/2 |
| 2004/0078215 A1 | 4/2004 | Dahlin | |
| 2004/0240720 A1 | 12/2004 | Brantley | |
| 2004/0243545 A1* | 12/2004 | Boone .................... | G16H 10/60 |
| 2005/0102140 A1 | 5/2005 | Davne et al. | |
| 2005/0137910 A1* | 6/2005 | Rao ........................ | G06Q 10/10 705/3 |
| 2005/0158767 A1* | 7/2005 | Haskell ................. | G16H 10/60 435/6.11 |
| 2005/0203775 A1 | 9/2005 | Chesbrough | |
| 2006/0020493 A1* | 1/2006 | Cousineau ............. | G06Q 50/22 705/2 |
| 2006/0020886 A1 | 1/2006 | Agrawal | |
| 2006/0041428 A1 | 2/2006 | Fritsch | |
| 2006/0122865 A1* | 6/2006 | Preiss ................. | G06Q 10/0633 705/2 |
| 2006/0129435 A1 | 6/2006 | Smitherman et al. | |
| 2006/0277073 A1 | 12/2006 | Heilbrunn | |
| 2007/0016450 A1 | 1/2007 | Bhora | |
| 2007/0016451 A1 | 1/2007 | Tilson | |
| 2007/0067185 A1 | 3/2007 | Halsted | |
| 2007/0106751 A1* | 5/2007 | Moore ................ | G06F 17/3089 709/217 |
| 2007/0118410 A1* | 5/2007 | Nadai ................... | G06Q 10/087 705/4 |
| 2007/0198907 A1* | 8/2007 | Degala ................ | G06F 17/2247 715/205 |
| 2007/0203708 A1* | 8/2007 | Polcyn .............. | H04M 3/42221 704/270.1 |
| 2007/0276649 A1* | 11/2007 | Schubert ............. | G06F 17/2276 704/2 |
| 2008/0077451 A1* | 3/2008 | Anthony ................ | G06Q 10/10 705/4 |
| 2009/0187407 A1* | 7/2009 | Soble ...................... | G10L 13/00 704/260 |
| 2009/0192800 A1* | 7/2009 | Brandt ........................ | 704/270.1 |
| 2009/0228299 A1 | 9/2009 | Kangarloo | |
| 2010/0138241 A1* | 6/2010 | Ruark .................... | G06Q 50/22 705/3 |
| 2010/0299135 A1 | 11/2010 | Fritsch | |
| 2012/0041950 A1* | 2/2012 | Koll ......................... | G09B 7/02 707/728 |
| 2012/0185275 A1 | 7/2012 | Loghmani | |
| 2014/0108047 A1 | 4/2014 | Kinney | |
| 2015/0088504 A1 | 3/2015 | Jagannathan | |
| 2016/0147955 A1 | 5/2016 | Shah | |
| 2016/0166220 A1 | 6/2016 | Bar-Shalev | |
| 2016/0179770 A1 | 6/2016 | Koll | |
| 2016/0267232 A1 | 9/2016 | Koll | |
| 2016/0335554 A1 | 11/2016 | Koll | |
| 2017/0270626 A1 | 9/2017 | Koll | |
| 2018/0040087 A1 | 2/2018 | Koll | |

FOREIGN PATENT DOCUMENTS

| | | |
|---|---|---|
| JP | 2006509295 A | 3/2006 |
| JP | 2008108021 A | 5/2008 |
| WO | 2005122002 | 12/2005 |
| WO | 2012048306 | 4/2012 |
| WO | 2012177611 | 12/2012 |

OTHER PUBLICATIONS

Daugherty B. et al., "Tracking Incidental Findings", Radiology Today, Jul. 2014, vol. 15, No. 7, p. 6.

OpenVPMS, Follow-up tasks, Submitted by Matt C on Fri, Sep. 17, 2010, Available at: https://openvpms.org/project/followup-task-lists-enhancements.

Yildiz M.Y. et al., "A text processing pipeline to extract recommendations from radiology reports", Journal of Biomedical Informatics, 2013, vol. 46, pp. 354-362.

* cited by examiner

DOCUMENT EXTENSION IN DICTATION-BASED DOCUMENT GENERATION WORKFLOW

BACKGROUND

A variety of automatic speech recognition (ASR) systems exist for recognizing speech and for generating text and/or commands based on such speech. ASR systems that generate text based on speech are typically referred to as "dictation" or "transcription" systems.

Some dictation systems allow users to dictate freeform text that is entered directly into documents exactly as spoken, except possibly with spelling corrections or other minor corrections applied. A common example of such systems is the dictation systems commonly used in conjunction with word processors to dictate memos, articles, and other prose documents. In contrast, some dictation systems are designed to generate and input data in a structured format based on the user's speech. For example, such an ASR system may be used to enter data into a database form, in which data in each field is constrained to have only certain values and to be represented in certain formats. For example, a "Priority" field in such a form may be associated with a dropdown list having only three values, such as "High," "Medium," and "Low," in which case the speech of a user dictating into such a field may be constrained to produce only one of these three possibilities as speech recognition results.

Whether the user provides input using speech input or other kinds of input (such as mouse or keyboard input), both freeform and structured input modalities have a variety of advantages and disadvantages. For example, one advantage of freeform input modalities is that they allow the user to provide a wide range of input and therefore to capture subtleties in the information provided. A corresponding disadvantage of structured input modalities is that by constraining the input options available to the user, they may fail to capture information that cannot accurately be represented using the available options.

One advantage of structured input modalities is that they require data to be stored in the form of discrete data elements that computers can act on easily and automatically. For example, if a patient has an allergy to allergen X and currently takes medication Y, if these two facts are input using structured input modalities (such as by using dropdown lists for selecting allergens and medications, respectively), then the resulting data can be encoded in discrete data elements representing allergen X and medication Y, respectively, and a computer can performing processing on such information easily and automatically, such as by comparing the data to contraindications on a predetermined list to determine whether allergen X is contraindicated with medication Y. Structured input modalities, in other words, enable data to be input in a form such that the meaning of the data is available to and unambiguously processable by a computer without the need for further interpretation. In contrast, data input using freeform input modalities (such as the text "the patient is allergic to X and is taking medication Y") must be parsed and interpreted in an attempt to discern the meaning of the text before a computer can attempt to parse the information represented by the text. Such parsing and interpretation are subject to errors which can impede the ability to perform the kind of processing that can be performed easily and automatically using data obtained using structured input modalities.

Another advantage of structured input modalities is that they can enable data to be input with fewer errors because the user is prevented, for example, from providing the wrong type of information (such as by inputting a name into a date field) or from providing information that is outside a permissible range of values (such as by entering −10 into a field representing the body temperature of a patient). A corresponding disadvantage of freeform input modalities is that they can allow input to contain a wide variety of errors because the user's input is not constrained.

Yet another advantage of freeform input modalities is that they do not predispose the user toward providing any one particular input over another. In contrast, structured input modalities can bias the input provided by the user towards the set or range of permitted inputs. This bias can be undesirable when the goal of the system is to faithfully capture and represent information. For example, a documentation system that only offers a checkbox as a means for inputting information about the presence or absence of a particular fact—such as whether a patient has hypertension—forces the user to pigeonhole the user's knowledge about the patient's condition into a binary value of "yes" or "no." If the user's knowledge of the patient indicates, for example, that the patient currently has mild hypertension, that the patient may possibly have hypertension, or that the patient is in the process of developing hypertension, then requiring the user to provide an answer of "yes" or "no" to the question, "Does the patient have hypertension?," will result in a misrepresentation of the true state of the patient in relation to hypertension.

Some input systems (such as EMR systems) attempt to address this problem by adding additional input choices, such as by enabling the user to provide not only binary answers to questions about facts, but also to provide information about additional qualities related to those facts, such as degree, likelihood, conditionality, and interdependency of such facts. For example, such a system might require the user to provide a "yes" or "no" answer to the question, "Does the patient have hypertension?," but also ask the user, in connection with that question, to provide a degree to which the user's "yes" or "no" answer is correct, a likelihood that the user's "yes" or "no" answer is correct, and so on.

Although this kind of solution can address some of the problems with structured input modalities, adding such additional input choices can quickly make using the system unwieldy due to the large amount and variety of inputs that the user must provide. Furthermore, the meanings of the additional input choices may not be clear to the users responsible for selecting such choices. For example, if the user is provided with choices of "Low," "Medium," and "High" for rating the likelihood that the patient has hypertension, it is not clear whether these choices represent equally-distributed probabilities such as 0-33.3%, 33.3-66.7%, and 66.7-100%, or some other ranges, such as 0-10%, 10-90%, and 90-100%. As a result, the user must make some decision about how to interpret the available input choices, and the result of that decision may differ both from that intended by the designer of the system and from the decisions made by other users when faced with the same set of input choices. As a result, the inputs provided by users may result in inaccurate information being entered into the system.

In light of these various advantages and disadvantages of freeform and structured input modalities, what is needed are improved techniques for capturing data to maximize accuracy and minimize errors.

SUMMARY

In one aspect, a method includes applying automatic speech recognition to an audio signal to produce a structured document representing contents of the audio signal. The method includes determining whether the structured document includes an indication of compliance with a best practice to produce a conclusion. The method includes inserting content into the structured document, based on the conclusion, to produce a modified structured document.

In another aspect, a system includes an automatic speech recognition system and a structured document analyzer. The automatic speech recognition system applies automatic speech recognition to an audio signal to produce a structured document representing contents of the audio signal. The automatic speech recognition system may include a structured document generator producing the structured document. The structured document analyzer determines whether the structured document includes an indication of compliance with a best practice to produce a conclusion and inserting content into the structured document, based on the conclusion, to produce a modified structured document.

Other features and advantages of various aspects and embodiments of the present invention will become apparent from the following description and from the claims.

BRIEF DESCRIPTION OF THE DRAWINGS

The foregoing and other objects, aspects, features, and advantages of the disclosure will become more apparent and better understood by referring to the following description taken in conjunction with the accompanying drawings, in which.

DETAILED DESCRIPTION

As described above, freeform and structured input modalities have a variety of advantages and disadvantages. In particular, it was mentioned that a structured input modality can bias the user toward providing the particular inputs that the structured input modality permits, thereby potentially causing inaccurate data to be generated. The bias imposed by structured input modalities, however, is not always harmful. In some circumstances it can have beneficial effects. For example, by forcing users to commit to certain discrete input choices, such as a particular diagnosis in the case of an electronic medical record, the resulting data may be less accurate but more unambiguous than it would have been if a freeform input modality had been used. Despite the potential decrease in accuracy that results from requiring input to be selected from among a discrete set of permissible inputs, forcing the user to make such a selection may cause the physician or other user to make the crucial decision about which discrete input to select early in the process (namely, at the time of providing the input), rather than leaving such a certain to the same user, or to a different and less qualified user, at a later date. As a result, the resulting data may be more likely to be useful for making accurate decisions without the need for further review or revision in certain circumstances, such as when the input data is to be used to submit a medical report to a payer for a treatment plan, if such payer requires specific diagnoses to be provided before payment can be made.

As another example, structured input forms can be useful for providing guidance to the user about the set of information that must be provided and about the possible contents of such information. For example, the presence of a form field containing the question, "Does the patient have hypertension?," can serve as a reminder to the user that the answer to such a question, and possibly other information related to the patient in connection with hypertension, is required. As a result, using forms to create documentation can result in fewer omissions of required or desirable information than using freeform text input. Because different forms can be used in different contexts and to create different kinds of documentation, forms can be tailored to prompt the user for the information that is relevant and/or required in each context. Therefore, one significant benefit of structured input modalities is that they can reduce the frequency of errors in the form of omissions of relevant and/or required data.

Embodiments of the present invention may be used to obtain the benefit of the advantages of both freeform and structured input modalities, while reducing or eliminating the disadvantages of both such input modalities.

Figure 1A:
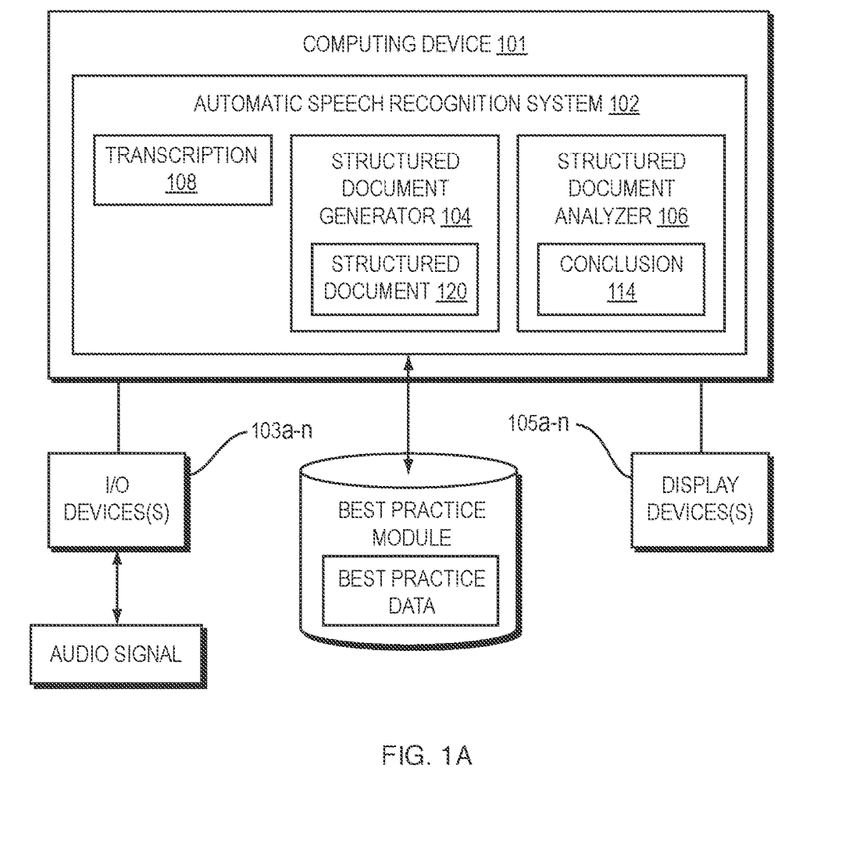
FIG. 1A is a block diagram depicting one embodiment of a system for document extension in dictation-based document generation workflow.
Figure 1B:
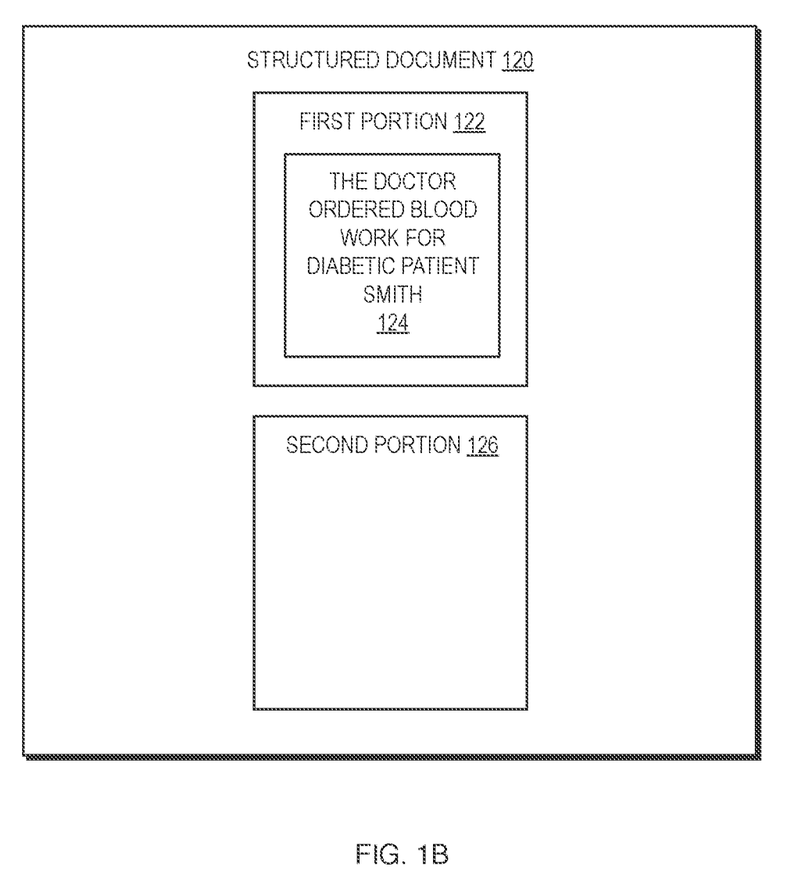
FIG. 1B is a block diagram depicting one embodiment of a structured document representing contents of an audio signal.
Figure 2:
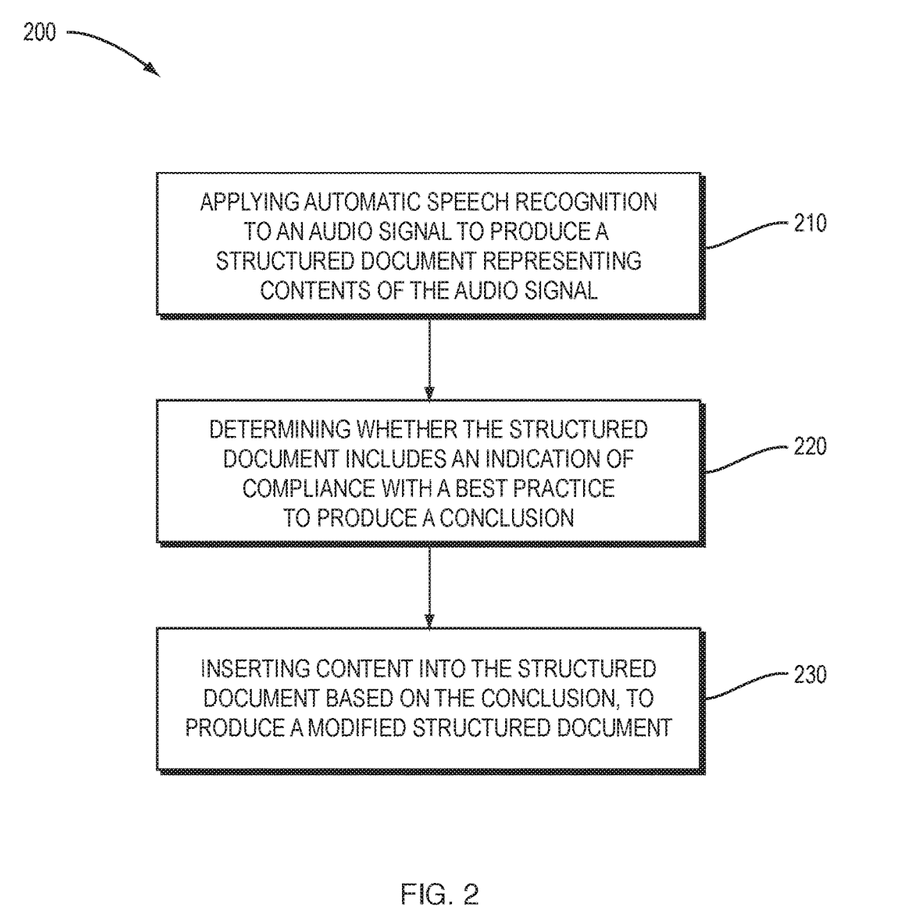
FIG. 2 is a flow diagram depicting one embodiment of a method for document extension in dictation-based document generation workflow.

Referring now to FIGS. 1A and 1B, in conjunction with FIG. 2, a method 200 includes applying automatic speech recognition to an audio signal to produce a structured document representing contents of the audio signal (210). In particular, embodiments of the present invention may enable users to dictate information in freeform, as if they were dictating a document to be transcribed into a freeform transcript. An automatic speech recognition system 102 may then be used to generate a structured document 120 based on the user's speech, where the structured document 120 encodes concepts from the user's speech into discrete data elements. For example, the automatic speech recognition system 102 may include a structured document generator 104 receiving an audio signal via an I/O device 103 (such as, for example, a microphone) and generating the structured document 120. As another example, the automatic speech recognition system 102 may generate a transcription 108 of the audio signal and provide the transcription 108 to the structured document generator 104 for generation of the structured document 120. As shown in FIG. 1B, the structured document 120 may include a plurality of portions (which may also be referred to as sub-templates, sub-portions or document components). A portion in the plurality of portions may or may not contain information—as shown in FIG. 1B, a first portion 122 contains information 124 (e.g., "The doctor ordered blood work for diabetic Patient Smith") but the second portion 126 does not contain any information. Examples of techniques that may be used to create such structured documents may be found, for example, in commonly-owned U.S. Pat. No. 7,584,103, entitled, "Automated Extraction of Semantic Content and Generation of a Structured Document from Speech"; commonly-owned U.S. Pat. No. 7,716,040, entitled, "Verification of Extracted Data"; and the patents, patent applications, and other documents cited therein. These techniques, however, are merely examples of techniques that may be used to generate a structured document 120 based on speech, and do not constitute limitations of the present invention.

The method 200 includes determining whether the structured document includes an indication of compliance with a best practice to produce a conclusion (220). For example, the automatic speech recognition system 102 may include, or be in communication with, a structured document analyzer 106 that analyzes the structured document 120 to determine whether the structured document 120 includes an indication of compliance with a best practice and produces a conclusion that represents the outcome of the determination. The structured document analyzer 106 may determine that the structured document 120 includes an indication of compliancy due to the presence of information within the structured document. Alternatively, for example, the structured document analyzer 106 may determine that the structured document 120 includes an indication of compliancy due to the absence of information within the structured document.

The structured document analyzer 106 may determine whether the form and/or content of the structured document 120 include the indication of compliance with the best practice (e.g., by determining whether the structured document 120 contains a particular section or piece of information); in such an embodiment, the structured document analyzer 106 may determine whether the contents of the structured document 120 comply with the best practice.

Additionally or alternatively, the structured document analyzer 106 may determine whether an action or other fact described by the structured document 120 complies with the best practice; in such an embodiment, the structured document analyzer 106 may determine whether a fact represented by the contents of the structured document 120 complies with the best practice. As an example, the structured document analyzer 106 may determine that to comply with a best practice, a particular structured document 120 should include an indication as to whether a foot examination was performed during a patient-physician encounter (e.g., the structured document 120 should include a statement such as "During the visit, Dr. Jones performed a foot examination for Patient Smith"); in determining that the structured document 120 includes no such indication, or that the structured document 120 includes an indication that no such examination occurred, the structured document analyzer 106 may produce a conclusion that the patient-physician encounter itself did not comply with the best practice since no foot examination was performed.

Once such a structured document 120 has been created, embodiments of the present invention may be used to automatically provide context-dependent guidance to encourage the use of best documentation practices by users of the system, such as the speaker whose speech was recognized to create the structured document 120 and/or other users who are responsible for editing, reformatting, and proofreading the document. For example, consider a case in which a user speaks into an audio capture device (such as a microphone connected to a desktop computer, or a handheld audio device containing an embedded microphone, or other input/output device 103) and in which the user has access to a computer monitor (or other display device 105) for reviewing and signing off on the resulting transcript. While (or after) the user dictates a freeform report into the audio capture device, any of the techniques referenced above may be used to generate a structured document 120 based on the user's speech. As another example, a user of a computing device 101b (not shown) may use an input/output device 103 to provide audio signals to the computing device 101b; the computing device 101b may transmit the audio signals to the computing device 101 shown in FIG. 1A.

An embodiment of the present invention may include or have access to information about best practices for use in connection with the report dictated by the user. Such best practices may, for example, include rules, guidelines, or preferences related to any one or more of the following:
information that must be included in the report (such as the patient's name and date of the patient's visit); and
actions that are required to be taken before the report can be completed (such as performing a particular procedure, such as a foot exam, on the patient during the visit described in the report).

Embodiments of the present invention may use a single set of best practices for all reports, or may use different sets of best practices to different reports. For example, a distinct set of best practices may apply to each of a plurality of report types and/or content. For any particular report, the set of best practices corresponding to the report's type (or corresponding to content in the report) may be applied to the report. As another example, a generic (e.g., universal) set of best practices may be applied to all reports in addition to specific sets of best practices based on report types and/or content. These and other examples may be combined with each other in any of a variety of ways.

The best practices may be represented and stored in any of a variety of ways, as will be understood by those having ordinary skill in the art. For example, best practices may take the form of rules that operate on discrete data elements in structured reports 120. For example, a best practice rule may dictate that if the discrete data elements in a structured report 120 indicate that the patient described by the report has diabetes, then the structured report 120 must indicate whether a foot exam was performed on the patient because it is a best practice to perform regular foot exams on diabetic patients. Such rules may operate on freeform text in addition to or instead of discrete data elements.

Best practices need not take the form of rules. Alternatively or additional for example, they may take the form of heuristics or procedures for drawing conclusions about whether a particular report is missing required (or recommended) data, includes data that it is prohibited from including (or that is advisable not to include), or otherwise fails to comply with or falls short of any required or desired standard applicable to the report.

The structured document analyzer 106 may identify a best practice based on data from a variety of sources, such as any one or more of the report itself, other reports (such as other reports related to the same patient or subject), database records (such as electronic medical records (EMRs)), or any other source of data. For example, the structured document analyzer 106 may analyze a data source relating to an event to which the structured document 120 relates to identify the best practice.

A structured report 120, once created, may be displayed to the user who dictated the report and/or to other users in any of a variety of ways. For example, the structured report 120 may be displayed as a document containing the text of the report, visually structured into sections (such as by adding section headings before each section or by emphasizing dictated section headings), and with discrete data elements (such as dates, medications, allergies, and diagnoses) emphasized or otherwise formatted to indicate that they are discrete data elements and/or to indicate the types of such discrete data elements. The structured report 120, in other words, may be rendered in a format that generally resembles that of a plain text document rendered by a conventional word processor, but with the structured elements of the document (e.g., sections and lower-level concepts) visually emphasized or otherwise indicated.

As mentioned above, the structured document analyzer 106 may produce a conclusion 114, such as a conclusion 114 that certain required information is missing from the report. Embodiments of the present invention may provide guidance to the user to provide input, such as additions to, deletions from, or modifications to the structured report 120 to cause the structured report 120 to conform to the best practices or to reduce the extent to which the structured report 120 fails to conform to the best practices.

Such guidance may be repeated for each of a plurality of best practices, and the kind and content of guidance may be the same or vary for each such best practice. Similarly, the same best practice may be applied multiple times to the same structured report 120, such as by applying the same best practice to multiple portions of the same structured report 120, thereby resulting in multiple instances of guidance within the same structured report 120 based on the same best practice.

Figure 1C:
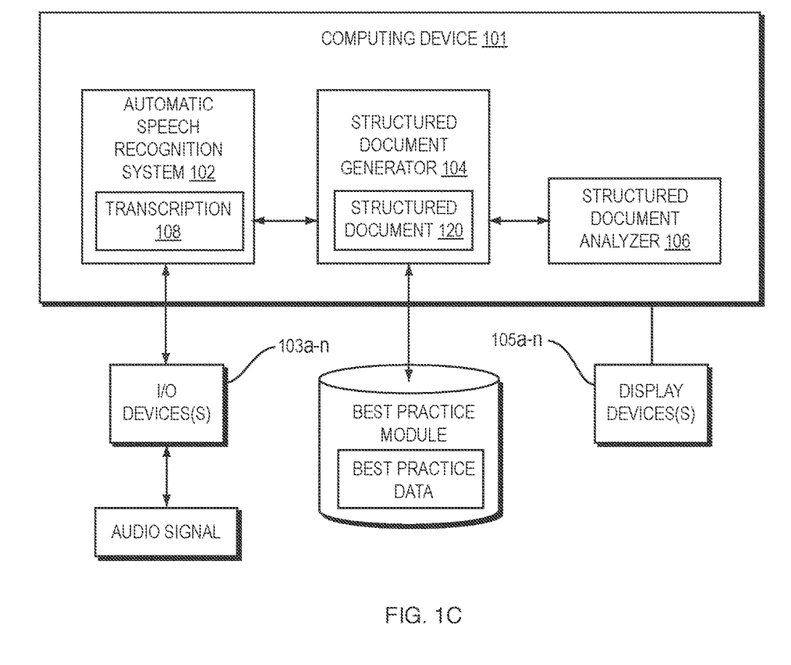
FIG. 1C is a block diagram depicting one embodiment of a system for document extension in dictation-based document generation workflow.
Figure 1D:
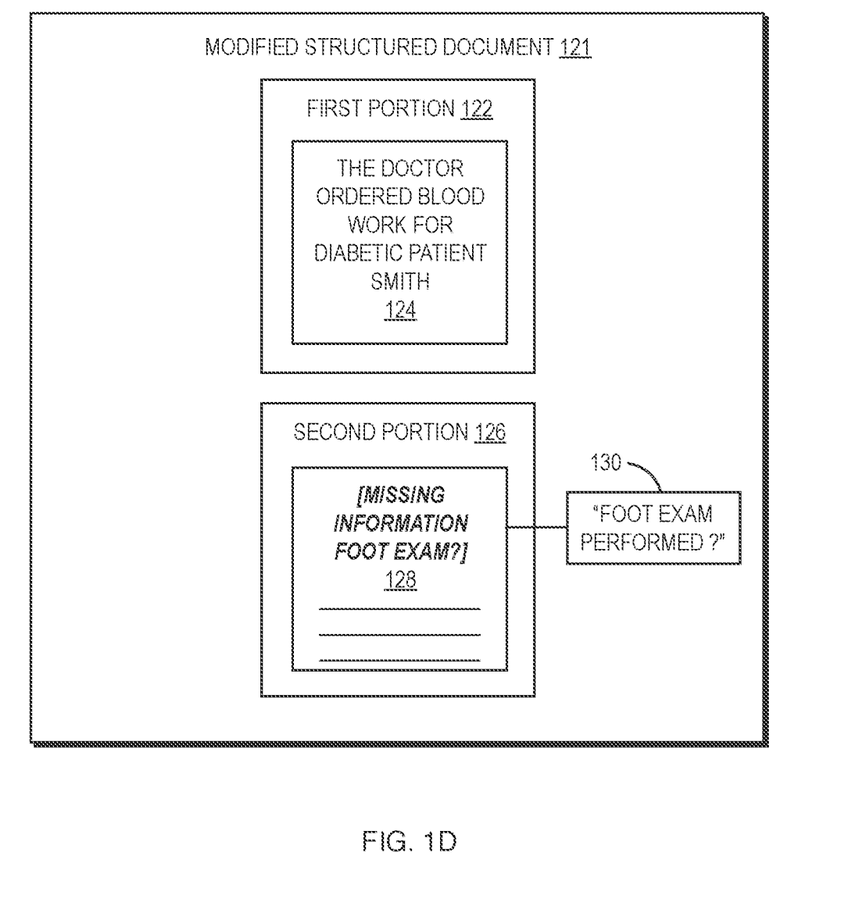
FIG. 1D is a block diagram depicting one embodiment of a structured document modified to request additional content.

The method 200 includes inserting content into the structured document, based on the conclusion, to produce a modified structured document (230). The automatic speech recognition system 102 may update the structured document 120 to include the user input; for example, the structured document generator 104 may include functionality for updating generated structured documents. In such an example, the structured document generator 104 may receive user input from the structured document analyzer 106 and update the structured document 120 with the user input. As another example, the structured document analyzer 106 may transmit an instruction to the structured document generator 104 to generate a prompt within the structured document 120. The structured document generator 104 may render the modified structured document for review by the user. FIG. 1D, described in greater detail below, provides an example of a modified structured document 121.

Although depicted in FIG. 1A as executing within the automatic speech recognition system 102, the structured document generator 104 and the structured document analyzer 106 may be provided as separate components in communication with the automatic speech recognition system 102. Referring now to FIG. 1C, and by way of example, the automatic speech recognition system 102 may transmit a transcription 108 of an audio signal to a stand-alone separate structured document generator 104, which in turn may transmit a structured document 120 to the structured document analyzer 106. In some embodiments, the structured document generator 104 and the structured document analyzer 106 may be provided as part of a report generation component (not shown); for example, the structured document generator 104 and the structured document analyzer 106 may be provided as plug-ins, add-ons or other extensions to software for generating components.

Embodiments of the present invention may provide output to the user to prompt the user to provide the input mentioned above for revising the structured report 120. Such prompting output may take any of a variety of forms. For example, a prompt (such as a window or a dialog box) that is distinct from the rendering of the report itself may be displayed to the user to prompt the user to provide input (e.g., by displaying the question "Was a foot exam performed on the patient?"). The user may provide such input in response to the distinct prompt, in response to which the system may update the structured report 120 accordingly (such as by adding a word, phrase, or sentence to the report representing the user's input, or by checking off an appropriate box in the report). The user may provide the input in freeform or in a structured form; for example, where the prompt includes an open-ended question, the user may provide the input in freeform. As an alternative example, when the prompt includes a closed question, the user may provide the input in a structured form. The form of the input provided in response to the prompt may differ from the form originally used to generate the structured document 120; for example, the structured document 120 may have been generated based on freeform speech, while the prompt may prompt for and receive input in the form of structured data, or vice versa.

As another example, a prompt may be displayed within the rendering of the report itself. Such a prompt may, for example, take the form of text appended to or inserted into the rendering of the report at an appropriate location. For example, if application of a best practice rule leads to the conclusion that the report is missing information about whether a foot exam was performed on the patient, and if the report contains a section on procedures performed on the patient during the current visit, then a prompt such as "Foot exam performed?" may be inserted into that section. The text input cursor may then be positioned immediately after this prompt, or the user may otherwise be notified of the prompt and given an opportunity to provide input directly into the document (such as by typing text) after the prompt.

Upon receiving input from the user, the system may update the report to include the input. For example, the system may insert the user input into the report substantially at or near the location of the prompt within the structured document 120; in such an example, the system may either maintain the prompt or remove the prompt from the location.

As another example, the prompt may take the form of a form field, such as a text field, check box, or dropdown list, into which the user may directly provide input in response to the prompt. An appropriate label (such as "Foot exam performed?") may be displayed near the form field to guide the user in providing input into the form field. The user may then provide input directly into the form field to cause the structured document 120 to be updated in accordance with the corresponding best practice. Referring to FIG. 1D, a block diagram depicts one example of a modified structured document 121. As shown in the example depicted in FIG. 1D, a modified structured document 121 may include a plurality of portions (which may also be referred to as sub-templates, sub-portions or document components). In the example shown in FIG. 1D, the modified structured document 121 is a version of the structured document 120 and includes the first portion 122, including information 124, and the second portion 126, which does not include any information. However, in the modified structured document 121, unlike in the structured document 120, the second portion 126 includes a prompt 128 and a label 130. The prompt 128 in this example is a text field into which a user may provide missing information. The label 130, displayed near the prompt 128, draws attention to the prompt 128 and provides guidance as to a type of information requested.

More generally, embodiments of the present invention may be contained within and/or operate in conjunction with a report generation procedure. Prompts provided by embodiments of the present invention may be part of and integrated into the report generation procedure. As a particular example, prompts may be integrated into the report itself. For example, as described elsewhere herein, as a report is being generated (and therefore after part of the report has been generated but before the entire report has been generated), any of the prompts disclosed herein may be provided to the user. Such prompts may be added or otherwise integrated into the report as the report is being generated. Similarly, input provided in response to such prompts may be added to or otherwise used to generate data that is added to the report as the report is being generated.

As one example of the above, a prompt may be a report sub-template, and such a sub-template may be inserted into the report while the report is being generated. A report sub-template may, for example, include one or more of a plurality of any kind(s) of form fields. For example, if an embodiment of the present invention determines that a particular portion of the report describes or otherwise relates to a particular type of medical procedure, in response to such a determination a report sub-template corresponding to the particular type of medical procedure may be identified and inserted into the report at the current location within the report. Such an inserted report sub-template may include content (e.g., text) that is added to the report and/or form fields (or other kinds of prompts) to obtain input from the user to insert into the report within the inserted report sub-template. The report sub-template and any data entered by users into the report sub-template may become part of the final report. As in the examples provided above regarding inserting, into the structured document 120, input provided in response to a prompt, the system may receive input from a user in response to the report sub-template and incorporate the user input into the report sub-template; and, as above, the system may determine to maintain or remove the prompt after the insertion of the user input. In examples in which the prompt is provided as a user interface element (e.g., a window displaying text, the window rendered as part of the report generation system), the system may determine whether to continue rendering the user interface element or to remove the user interface element from a display after the user input has been received.

As described above, the system may prompt the user to provide input representing missing information. For example, when a best practice indicates that a particular type of content (such as a particular concept, e.g., report section or fact) should be included in a particular type of report, but the structured document analyzer 106 determines that the structured document 120 does not contain the particular type of content, the content is said to be missing from the report. By way of example, if a best practice requires that a type of report include information indicating that a foot examination was performed on a patient but the structured document 120 does not include information indicating that a foot exam was performed, then information relating to a foot exam is said to be "missing" from the report.

However, embodiments of the present invention are not limited to prompting the user to provide input representing missing information. As another example, embodiments of the present invention may automatically update the structured report 120 with the missing information, an estimate of the missing information, or an indication that such information is missing, without receiving input from the user. For example, if the structured document analyzer 106 determines that to comply with a particular best practice, the report is required to indicate whether a foot exam was performed and the report does not indicate whether a foot exam was performed, embodiments of the present invention may take any of a variety of actions, such as updating the report to indicate that no information is available about whether a foot exam was performed (e.g., by inserting the text "Foot exam performed? No information available"), or by retrieving information about whether a foot exam was performed from an electronic medical record associated with the same patient and inserting that information automatically into the report (e.g., by inserting the text "Foot exam performed? Yes") into the report. As another example, the system may prompt a user to take an action. For instance; the structured document analyzer 106 may determine whether a fact represented by the structured document 120 complies with the best practice; if the described facts are determined not to comply with the best practice, then the system may prompt the user to take an action that complies with the best practice. As an example, the system may prompt a reviewer of the structured document 120 to perform a foot exam in an embodiment in which the structured document 120 is being generated during a patient visit; the system may also prompt a reviewer of the structured document 120 to schedule, or arrange to have scheduled, a follow-up appointment with a patient to take an additional action (such as to perform a foot exam). The system may also prompt a reviewer of the structured document 120 to follow up with a practitioner to determine how to address the missing information (for example, a user reviewing the structured document 120 may be prompted to contact the physician who originally generated the audio signals and determine how the physician prefers to obtain the missing information or complete an incomplete task). In some embodiments, therefore, the system prompts a human user to take an action, receives input from the human user, the input indicating a status of the action, and inserts the input as content into the structured document 120. As with the examples above, such automatically generated information could be inserted into the structured report 120 in other ways, such as by inserting it into form fields or using it to provide input to user interface controls such as checkboxes or dropdown lists.

Any information inserted automatically into a report may be marked as "automatically generated." When the report is rendered, such automatically generated information may be flagged as such, such as by highlighting such information in a particular color, to call attention to the fact that such information was generated automatically and not input manually by a human. The user may even be specifically prompted to review and, if necessary, edit such information.

Any of the techniques described above may be performed while a particular report is being transcribed or after the report has been transcribed. For example, after a particular portion of a report has been transcribed, best practices may be applied to that portion of the report in any of the ways disclosed above, even as the user continues to dictate additional portions of the report and even as such portions are transcribed to generated additional text.

Furthermore, any of the techniques described above may be used in connection with a single user or multiple users across any number of computing devices. For example, a single user may dictate a report and also provide additional input in response to prompts generated based on application of best practices to the report. As another example, a first user may dictate the report and a second user may provide additional input in response to prompts generated based on application of best practices to the report.

Embodiments of the present invention have a variety of advantages. For example, embodiments of the present invention combine some of the advantages of freeform input modalities with some of the advantages of structured input modalities, while reducing or eliminating some of the disadvantages of both. In particular, embodiments of the present invention combine the ability of freeform input modalities to enable users to provide unbiased and nuanced input with the ability of structured input modalities to enforce requirements that certain kinds of data be input. One way in which embodiments of the present invention achieve this result is by enabling the user to first provide input using a freeform input modality, then determining whether the input includes an indication of compliance with one or more best practices, and then extending the resulting report (either automatically or based on additional input from the user) based on conclusions drawn from the determination. The report extension may involve obtaining input from the user using a structured input modality, such as by obtaining input from the user in a form field. By requesting and obtaining such structured input from the user only if an when necessary, embodiments of the present invention avoid predisposing the user toward providing input that is biased in the way caused by conventional structured input modalities.

Another benefit of embodiments of the present invention is that they may increase the accuracy of the resulting report, either by guiding the user toward providing more complete information that is compliant with best practices, or by obtaining and inserting such information into the report automatically. Reduced errors and higher degrees of completeness can be particularly beneficial in contexts, such as medical reporting, in which the accuracy and completeness of reports can have an impact on human health and safety, and in which accurate and complete reports are necessary to comply with regulations and to obtain reimbursement for the procedures that resulted in the reports.

Yet another advantage of embodiments of the present invention is that by reminding a physician and/or other user to take a recommended or required action (such as performing a procedure on a patient), the user can be reminded to take such action and thereby be more likely to take the action. Even if the user is reminded of the action to take at a time when it is no longer possible to take the action in connection with the event that led to the creation of the report (such as a patient visit), the user may be reminded of the need to take the action in similar circumstances in the future. In this way, embodiments of the present invention may serve to educate users and to increase the likelihood that they will take recommended and/or required actions in the future.

Another advantage of embodiments of the present invention is that they may be used to encourage or require users to provide input that is useful and/or required for subsequent processing, such as information that is required to generate a bill for reimbursement of healthcare services. For example, if a report is input solely in the form of freeform text using conventional methods, it might be difficult to extract information needed for billing from such text. For example, if a freeform text report describes a surgery performed on a patient and, in the course of describing the surgery, describes not only stents that actually were inserted into the patient but also stents that were attempted to be inserted into the patient without success, it might be difficult or impossible to automatically extract from such a report the number of stents that actually were inserted into the patient. Yet it may be necessary to provide such a number to generate a bill that may be used to obtain reimbursement for the surgery. If instead, using embodiments of the present invention, the physician or other user is required to provide the number of stents actually inserted as a discrete data element using a structured input modality, then the bill may be generated automatically because the system has enforced the requirement that information necessary to generate the bill be provided as input. The same logic applies to any information that is contained within a document but is difficult to extract discretely and automatically.

Yet another benefit of embodiments of the present invention is that they may be used to reconcile existing stored data (such as discrete data, e.g., data stored in an EMR or other database record) with data input into a report. For example, if the dictating physician indicates that a patient has uncontrolled diabetes and existing data (e.g., data for the patient stored in an EMR) already indicates that the patient has diabetes but does not indicate whether the diabetes is uncontrolled, embodiments of the present invention may be used to revise the existing data (e.g., EMR) about the patient to specify that the patient's diabetes is uncontrolled.

It is to be understood that although the invention has been described above in terms of particular embodiments, the foregoing embodiments are provided as illustrative only, and do not limit or define the scope of the invention. Various other embodiments, including but not limited to the following, are also within the scope of the claims. For example, elements and components described herein may be further divided into additional components or joined together to form fewer components for performing the same functions.

The techniques described above may be implemented, for example, in hardware, software tangibly stored on a computer-readable medium, firmware, or any combination thereof. The techniques described above may be implemented in one or more computer programs executing on a programmable computer including a processor, a storage medium readable by the processor (including, for example, volatile and non-volatile memory and/or storage elements), at least one input device, and at least one output device. Program code may be applied to input entered using the input device to perform the functions described and to generate output. The output may be provided to one or more output devices.

Each computer program within the scope of the claims below may be implemented in any programming language, such as assembly language, machine language, a high-level procedural programming language, or an object-oriented programming language. The programming language may, for example, be a compiled or interpreted programming language.

Each such computer program may be implemented in a computer program product tangibly embodied in a machine-readable storage device for execution by a computer processor. Method steps of the invention may be performed by a computer processor executing a program tangibly embodied on a computer-readable medium to perform functions of the invention by operating on input and generating output. Suitable processors include, by way of example, both general and special purpose microprocessors. Generally, the processor receives instructions and data from a read-only memory and/or a random access memory. Storage devices suitable for tangibly embodying computer program instructions include, for example, all forms of non-volatile memory, such as semiconductor memory devices, including EPROM, EEPROM, and flash memory devices; magnetic disks such as internal hard disks and removable disks; magneto-optical disks; and CD-ROMs. Any of the foregoing may be supplemented by, or incorporated in, specially-designed ASICs (application-specific integrated circuits) or FPGAs (Field-Programmable Gate Arrays). A computer can generally also receive programs and data from a storage medium such as an internal disk (not shown) or a removable disk. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium.

What is claimed is:

1. A computer-implemented method performed by at least one computer processor, the method comprising:
    (A) applying automatic speech recognition to an audio signal to produce a structured document representing contents of the audio signal;
    (B) determining whether the structured document includes an indication of compliance for each of a plurality of best practices to produce a conclusion, the plurality of best practices related to at least one action required to be taken before completion of the structured document, at least one of the plurality of best practices including at least one of a heuristic and a procedure for drawing a conclusion about whether the structured document fails to comply with a standard applicable to the structured document; and
    (C) inserting content into the structured document, based on the conclusion, to produce a modified structured document, wherein inserting further comprises:
        (C)(1) obtaining the content from a data source without human input; and
        (C)(2) inserting the content into the structured document.

2. The method of claim 1, wherein (B) further comprises: identifying a type of the structured document;
    identifying one of the plurality of best practices associated with the identified type; and
    determining whether the structured document includes an indication of compliance with the identified one of the plurality of best practices to produce the conclusion.

3. The method of claim 2, further comprising determining whether the structured document includes an indication of compliance with a universal best practice.

4. The method of claim 1, wherein (B) further comprises:
    analyzing a data source relating to an event to which the structured document relates; and
    identifying the best practice based on the analysis of the data source.

5. The method of claim 1, further comprising producing a conclusion that information is missing from the structured document.

6. The method of claim 1, wherein (C) comprises:
    (C)(1) obtaining a version of the content from a data source without human input; and
    (C)(2) inserting the version of the content into the structured document with an indication that the version of the content is an estimate of the content.

7. The method of claim 1, wherein (C) comprises:
    (C) inserting, into the structured document, an indication that the content is missing.

8. The method of claim 1, wherein (C) comprises:
    (C)(1) obtaining the content from a data source without human input; and
    (C)(2) inserting the content into the structured document with an indication that the content was automatically generated.

9. The method of claim 8, further comprising inserting, into the structured document, a request for review of the automatically generated content.

10. The method of claim 1, wherein (A) comprises applying automatic speech recognition to a first portion of the audio signal to produce a structured document representing contents of the first portion of the audio signal, during generation of a second portion of the audio signal.

11. A non-transitory computer readable medium having instructions stored thereon, wherein the instructions are executable by at least one computer processor to perform a method, the method comprising:
    (A) applying automatic speech recognition to an audio signal to produce a structured document representing contents of the audio signal;
    (B) determining whether the structured document includes an indication of compliance for each of a plurality of best practices to produce a conclusion, the plurality of best practices related to at least one action required to be taken before completion of the structured document, at least one of the plurality of best practices including at least one of a heuristic and a procedure for drawing a conclusion about whether the structured document fails to comply with a standard applicable to the structured document; and
    (C) inserting content into the structured document, based on the conclusion, to produce a modified structured document, wherein inserting further comprises:
        (C)(1) obtaining the content from a data source without human input; and
        (C)(2) inserting the content into the structured document.

12. The computer readable medium of claim 11, wherein (B) further comprises: identifying a type of the structured document; identifying a best practice associated with the identified type; and determining whether the structured document includes an indication of compliance with the identified best practice to produce the conclusion.

13. The computer readable medium of claim 12, further comprising determining whether the structured document includes an indication of compliance with a universal best practice.

14. The computer readable medium of claim 11, wherein (B) further comprises: analyzing a data source relating to an event to which the structured document relates; and identifying the best practice based on the analysis of the data source.

15. The computer readable medium of claim 11, further comprising producing a conclusion that information is missing from the structured document.

16. The computer readable medium of claim 11, wherein (C) comprises:
    (C)(1) obtaining a version of the content from a data source without human input; and
    (C)(2) inserting the version of the content into the structured document with an indication that the version of the content is an estimate of the content.

17. The computer readable medium of claim 11, wherein (C) comprises: (C) inserting, into the structured document, an indication that the content is missing.

18. The computer readable medium of claim 11, wherein (C) comprises:
    (C)(1) obtaining the content from a data source without human input; and
    (C)(2) inserting the content into the structured document with an indication that the content was automatically generated.

19. The computer readable medium of claim 18, wherein the method further comprises inserting, into the structured document, a request for review of the automatically generated content.

20. The computer readable medium of claim 11, wherein (A) comprises applying automatic speech recognition to a first portion of the audio signal to produce a structured document representing contents of the first portion of the audio signal, during generation of a second portion of the audio signal.

* * * * *